US00PP27389P3

(12) United States Plant Patent
Suphachadiwong

(10) Patent No.: US PP27,389 P3
(45) Date of Patent: Nov. 15, 2016

(54) *VANDA* PLANT NAMED 'SPCDW1310'

(50) Latin Name: ***Vanda* hybrid**
Varietal Denomination: SPCDW1310

(71) Applicant: Thumrong Suphachadiwong, Chonburi (TH)

(72) Inventor: Thumrong Suphachadiwong, Chonburi (TH)

(73) Assignee: Suphachatwong Innovation (TH)

( * ) Notice: Subject to any disclaimer, the term of this patent is extended or adjusted under 35 U.S.C. 154(b) by 75 days.

(21) Appl. No.: 14/120,925

(22) Filed: Jul. 9, 2014

(65) Prior Publication Data

US 2015/0020263 P1 Jan. 15, 2015

(30) Foreign Application Priority Data

Jul. 10, 2013 (QZ) ..... PBR 2013/1920

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Susan McCormick Ewoldt
(74) *Attorney, Agent, or Firm* — Cassandra Bright

(57) ABSTRACT

A new and distinct *Vanda* cultivar named 'SPCDW1310' is disclosed, characterized by unique flower coloration of violet with small specks of white and large flower size. The new variety is a *Vanda*, typically produced as an indoor ornamental plant.

1 Drawing Sheet

Latin name of the genus and species: *Vanda* hybrid.
Variety denomination: 'SPCDW1310'.

BACKGROUND OF THE INVENTION

This application relates to a new cultivar of *Vanda* hybrid. The new variety is the product of a planned breeding program. The new variety originated as a seedling from the crossing of the unpatented, proprietary seed parent *Vanda* 'K42RB' with the unpatented, proprietary pollen parent referred to as *Vanda* 'JB4N'. The crossing was made by the inventor in his research greenhouse in Chonburi, Thailand in December of 2000.

The new variety was first selected by the inventor, Thumrong Suphachadiwong, a citizen of Thailand, in February of 2006 in a research greenhouse belonging to the inventor in Chonburi, Thailand. After identifying the new variety as a potentially interesting selection, the inventor continued confidential testing and propagation of 'SPCDW1310', assessing stability of the unique characteristics of this variety.

Asexual reproduction of the new cultivar 'SPCDW1310' was first performed at a commercial laboratory belonging to the inventor in Chonburi, Thailand by tissue culture in June of 2007. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SPCDW1310' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1310.' These characteristics in combination distinguish 'SPCDW1310' as a new and distinct *Vanda* cultivar:

1. Unique flower coloration of violet with small specks of white.
2. Large flowers.

PARENT COMPARISON

Although the inventor has records of the name of the seed parent, *Vanda* 'K42RB' he no longer has record of the phenotypic characteristics of the seed parent. Comparison cannot be made.

Although the inventor has records of the name of the pollen parent, *Vanda* 'JB4N' he no longer has record of the phenotypic characteristics of the seed parent. Comparison cannot be made.

COMMERCIAL COMPARISON

'SPCDW1310' is similar in most horticultural characteristics to the unpatented commercial variety *Vanda* 'SPCDDW1109' in most horticultural characteristics. However the new variety, 'SPCDW1310' differs from 'SPCDDW1109' in the following characteristics:

1. The new variety has violet flowers with small white specks. The comparator variety has a light yellow background coloration with dark purple spots and a violet margin.
2. Different lateral sepal shape.
3. Narrower lips.

'SPCDW1310' is similar in most horticultural characteristics to the unpatented commercial variety *Vanda* 'Exotic Purple' in most horticultural characteristics. However the new variety, 'SPCDW1310' differs from 'Exotic Purple' in the following characteristics:

1. Darker flower color.
2. Sepals and petals have less white coloration.
3. Leaves are more upright.
4. Different lip shape.

BRIEF DESCRIPTION OF THE PHOTOGRAPH

The accompanying photograph in FIG. 1 illustrates in full color a typical plant of 'SPCDW1310' grown in a commercial greenhouse in Honselersdijk, the Netherlands. The plant is 5½ to 6½ years old. Described plant is in a hanging basket without soil. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SPCDW1310' plants grown in a commercial greenhouse in Honselersdijk, the Netherlands. The plant is 5½ to 6½ years old. Described plant not container-grown, but in a hanging basket without soil. Temperatures ranged between 19° C. and 23° C. day and night. No photoperiodic or chemical treatments were given to the plants. During bright Summer conditions, shade was given. During dark Winter months, no supplemental light was given. Measurements and numerical values represent averages of typical plant types.

Botanical classification: *Vanda* hybrid 'SPCDW1310'.

PROPAGATION

Type of propagation typically used: Tissue culture.

Time to produce a rooted cutting/liner: The time needed from for the start of a mericlone to get the small plants ready for deflasking is approx. 24 months under a controlled temperature of about 26 degrees Celsius. After that period they have matured roots. They start to make roots in the last 6 months in flasks. After deflasking they remain in shade under local outdoor temperatures.

Root description: Moderately to heavy rooting with aerial roots only. Roots very fleshy, non-fibrous. Average length of old roots: 34.3 cm, average diameter of old roots: 0.3 mm, average diameter of young roots: 0.6 cm. Old roots colored yellow-green; near RHS 146D. Young roots colored greyed-green; near RHS 192C and 192D, growing tips of roots yellow-green; 152A.

PLANT

Growth habit: Monopodial, upright.

Height to top of foliage: Average height from base (plant grown in hanging basket, so no soil line present) to top of foliage: 41.5 cm.

Height to top of flowers: Average height from base (plant grown in hanging basket, so no soil line present) to top of flowers: 52.8 cm.

Plant spread: Average: 40.9 cm.

Normal pot size: Hanging basket (8×8 cm square).

Growth rate: Moderate.

Number of leaves per plant: Average: 20.

FOLIAGE

Leaf:

- *Arrangement*.—Distichous.
- *Average length*.—Approximately 25.8 cm.
- *Average width*.—Approximately 2.6 cm.
- *Shape of blade*.—Ligulate, strongly carinate.
- *Aspect*.—Slightly curved.
- *Apex*.—Unequal praemorse.
- *Base*.—Sheathing. Sheath length: Average 1.8 cm. Sheath width: Average 1.2 cm. Sheath color: Yellow-green; near RHS 144A.
- *Margin*.—Entire.
- *Texture of top surface*.—Glabrous, matte.
- *Texture of bottom surface*.—Glabrous, matte.
- *Color*.—Young foliage upper side: Green; near RHS 143B. Young foliage under side: Green; near RHS 143A. Mature foliage upper side: Green to yellow-green; in between RHS N137B and 147A. Mature foliage under side: Yellow-green; near RHS 146B.
- *Venation*.—Type: Parallel. Venation coloration: As leaf surface; upper side green to yellow-green; in between RHS N137B and 147A, lower side yellow-green; near RHS 146B.

Petiole: No petioles present, leaves sessile.

FLOWERING CHARACTERISTICS

Flower bud:

- *Rate of opening*.—Buds open approx. three weeks from first appearance.
- *Length*.—Average: 1.4 cm.
- *Diameter*.—Average: 1.5 cm.
- *Shape*.—Broad obovate.
- *Color*.—Greyed-purple; near RHS N187A, base yellow-green; near RHS 145D, dotted greyed-purple; N187B and N187C.

Peduncle:

- *Length*.—Approximately 34.0 cm.
- *Width*.—Approximately 0.6 cm.
- *Aspect*.—Approximately 30° angle to rosette.
- *Strength*.—Strong.
- *Texture*.—Smooth, moderately glossy.
- *Color*.—Green to yellow green; in between RHS 143B and 144A.

Inflorescence:

- *Flowers per stem*.—Average: 10.
- *Inflorescence arrangement*.—Axially placed raceme.
- *Inflorescence height*.—Approximately 20.3 cm (measured from base of lowest flower to top of upper flower).
- *Inflorescence width*.—Approximately 18.5 cm.

Individual flowers:

- *Flower type*.—Zygomorphic (orchidaceous), typical shape for the genus *Vanda*.
- *Shape*.—Zygomorphic, consisting of three sepals and three petals, one of which is transformed into a labellum (lip).
- *Length* (*height*).—Approximately 10.5 cm.
- *Width*.—Approximately 9.6 cm.
- *Depth*.—Approximately 3.4 cm.

*Fragrance*.—No fragrance.
*Persistent*.—No.
*Quantity of petals*.—3 petals, 2 "traditional" petals and a labellum (lip), described separately).
*Petals*.—Arrangement: one lateral petal on each side. Length: Approximately 4.7 cm. Width: Approximately 4.3 cm. Shape: Near orbicular to broad ovate. Apex: Obtuse. Base: Cuneate. Margin: Entire, slightly undulate. Texture: Upper forward surface: Glabrous, matte, velvety. Texture: Lower back surface: Glabrous, matte, velvety. Color: When opening, forward surface: White; near RHS NN155B, slightly darker towards the top; near N155A, petal heavily dotted violet; near RHS 83A. When opening, back surface: White; near RHS 155C, lightly tinged violet and yellow-green; near RHS 85D and 145D, darker towards the top; near 85B, petal moderately dotted violet; near RHS 83D. Fully Opened, forward surface: Violet; in between RHS 86C and 86D and N87C to N87D, darker towards the margins and top; near RHS 86B, base streaked white; near RHS N155A. Small specks of white N155A occurring closer to base, infrequently towards margins. Fully Opened, back surface: Violet; in between RHS 86C and 86D and N87C to N87D, darker towards the margins and top; near RHS 86B, base white; near RHS N155A. Fading, forward surface: Not fading. Fading, back surface: Not fading.
*Color venation fully opened, forward surface*.—Veins not visible, colored as petal surface.
*Color venation fully opened, back surface*.—Main veins violet; near RHS N87C to N87D, other veins as petal surface.

Labellum/lip:
*Shape*.—Three-lobed, lateral lobes involute, central lobe slightly revolute.
*Length*.—Approximately 2.0 cm.
*Width*.—Approximately 1.7 cm.
*Texture*.—Glabrous, slightly glossy, with 3 callosities.
*Tip*.—Emarginate.
*Base*.—Cuneate.
*Color*.—When opening, forward surface: Lateral lobes violet; near RHS 84C to 84D, striped darker; near RHS 83A, with an orange basal spot; near RHS 26A. Central lobe and callosities violet; near RHS 83A and 86A, base violet-blue; near RHS N92A, bases of callosities violet; near RHS 84D. When opening, back surface: Lateral lobes violet; near RHS 84C to 84D, striped darker towards the base; near RHS N87A and N87B. Central lobe violet; near RHS 86A, top slightly darker, base white; near RHS 155C. Fully Opened, forward surface: Lateral lobes violet; near RHS 84C and 84D, striped darker; near RHS 83A, with an orange basal spot; near RHS 26A. Central lobe and callosities violet; near RHS 86A, base and top darker violet to violet-blue; in between near RHS 86A and N92A, bases of callosities violet; near RHS 84D. Fully Opened, back surface: Lateral lobes violet; near RHS 84C and 84D, striped darker towards the base; near RHS N87A and N87B. Central lobe violet; near RHS 86A and 86B, top slightly darker, base white; near RHS 155C. Fading, forward surface: Not fading. Fading, back surface: Not fading.
*Color venation fully opened, forward surface*.—No venation visible on labellum.
*Color venation fully opened, back surface*.—No venation visible on labellum.
*Margin*.—Entire.

Spurs:
*Quantity*.—Average: 1.
*Appearance*.—Short triangular, in line with central lobe of labellum.
*Length*.—Approximately 0.8 cm.
*Width*.—Approximately 0.5 cm.
*Height*.—Approximately 0.7 cm (at the base).
*Shape*.—Short triangular.
*Apex*.—Obtuse.
*Base*.—Broad cuneate.
*Margin*.—Entire.
*Texture*.—Glabrous, very slightly glossy.
*Color*.—White: near RHS 155C, striped greyed-purple; near RHS N187D.

Sepals:
*Quantity*.—Average: 3.
*Appearance*.—One dorsal sepal (pointing upright) and two lateral sepals.
*Length*.—Dorsal and lateral sepals approximately 5.0 cm.
*Width*.—Dorsal sepal approximately 4.6 cm. Lateral sepals approximately 5.7 cm.
*Shape*.—Dorsal sepal broad ovate to near orbicular. Lateral sepals near orbicular to reniform.
*Apex*.—Obtuse.
*Base*.—Cuneate.
*Margin*.—Entire.
*Texture*.—Glabrous, matte, velvety.
*Color*.—Dorsal sepal white; near RHS NN155D, violet towards the top; near N87B, N87C and N88B, petal heavily dotted violet; near RHS 83A and 83B. Lateral sepals white; near RHS 155A, 155B and 155C, top and margins violet; N88C and N88D, heavily dotted violet and violet-blue; near RHS 86A and N92A.

Pedicels:
*Length*.—Approximately 5.6 cm.
*Diameter*.—Approximately 0.55 cm.
*Angle*.—Approximately 65° angle to peduncle.
*Strength*.—Very strong.
*Texture*.—Glabrous, axially angled with 5 "ribs", axially twisted (due to resupination), glossy.
*Color*.—Violet; near RHS 85C and 85D, tinged near RHS 84C towards distal end, tinged yellow-green; near RHS 145C to 145D towards proximal end.

REPRODUCTIVE ORGANS

*Stamens, style and stigma fused into column*?.—Yes.
*Column length*.—Approximately 0.7 cm.
*Column diameter*.—Approximately 0.7 cm.
*Column color*.—White; near RHS NN155A, upper side tinged violet; 84D.
*Ovary*.—Position: Inferior. Diameter: Approximately 0.5 cm. Color: White; near RHS 155A.
*Pollinia color*.—Yellow-orange; near RHS 14A.

OTHER CHARACTERISTICS

Disease resistance: Neither resistance nor susceptibility to the normal diseases found in *Vanda* has been observed.

Drought tolerance and cold tolerance: Tropical Orchid, does not tolerate cold or drought.

Fruit/seed production: No fruits/seeds detected to date.

What is claimed is:

1. A new and distinct cultivar of *Vanda* plant named 'SPCDW1310' as herein illustrated and described.

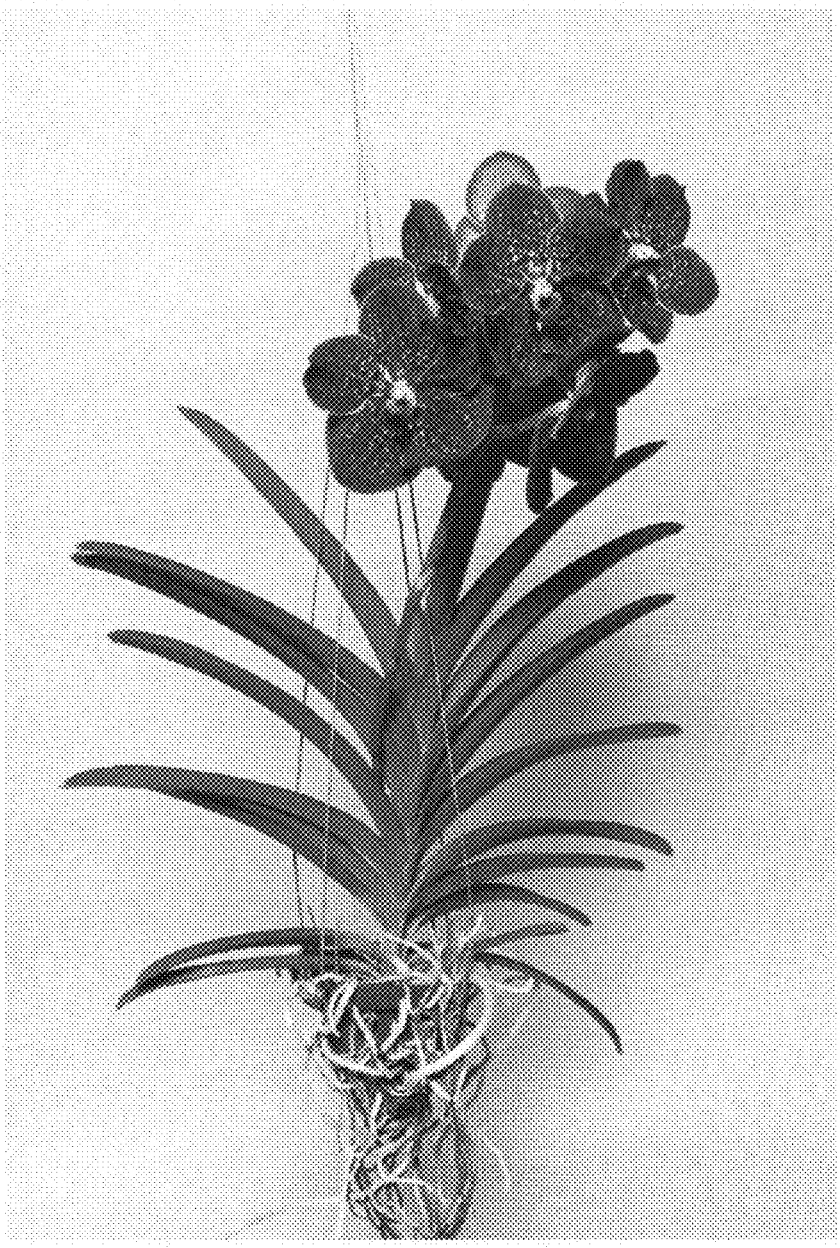

* * * * *